US00PP29954P3

(12) United States Plant Patent
Madsen

(10) Patent No.: US PP29,954 P3
(45) Date of Patent: Dec. 4, 2018

(54) ***CAMPANULA* PLANT NAMED 'PKM06'**

(50) Latin Name: ***Campanula* hybrid**
Varietal Denomination: PKM06

(71) Applicant: Gartneriet PKM A/S, Odense N (DK)

(72) Inventor: Christian Hald Madsen, Korsør (DK)

(73) Assignee: Gartneriet PKM A/S, Odense N (DK)

( * ) Notice: Subject to any disclaimer, the term of this patent is extended or adjusted under 35 U.S.C. 154(b) by 88 days.

(21) Appl. No.: 15/330,523

(22) Filed: Oct. 3, 2016

(65) Prior Publication Data

US 2018/0098478 P1 Apr. 5, 2018

(51) Int. Cl.
*A01H 5/02* (2018.01)

(52) U.S. Cl.
USPC ..... Plt./414
CPC ..... *A01H 5/02* (2013.01)

(58) Field of Classification Search
USPC ..... Plt./414
See application file for complete search history.

(56) References Cited

PUBLICATIONS

UPOV hit on *Campanula* plant named 'PKM06', QZ PBR 20161610, application date Jun. 28, 2016.*
Printout of application information from PLUTO Plant Variety Database for corresponding Canadian application No. 16-9027 filed Oct. 4, 2016 (1 page) (http://www.wipo.int/pluto).
Printout of application information from PLUTO Plant Variety Database for corresponding CPVO application No. 2016/1610 filed Jun. 28, 2016 (1 page) (http://www.wipo.int/pluto).

* cited by examiner

*Primary Examiner* — Anne Marie Grunberg
(74) *Attorney, Agent, or Firm* — Foley & Lardner LLP

(57) ABSTRACT

A new and distinct cultivar of *Campanula* plant named 'PKM06', characterized by its compact plant habit; globular plant form; vigorous growth habit; double/filled light violet-blue flowers and small leaves.

3 Drawing Sheets

Latin name of genus and species of the plant claimed: *Campanula* hybrid.

Variety denomination: 'PKM06'.

BACKGROUND OF THE INVENTION

The present invention relates to a new and distinct cultivar of *Campanula* hybrid plant, and hereinafter referred to by the name 'PKM06'.

The new *Campanula*, 'PKM06', is a product of a planned breeding program conducted by the inventor, Christian Hald Madsen, in Søhus, Denmark. The new *Campanula* originated from a planned cross between two *Campanula* hybrids; the female parent being an unnamed, proprietary *Campanula* variety (unpatented) and the male parent being an unnamed, proprietary *Campanula* variety (unpatented). The initial crossing was performed in April 2014 by the Inventor in Søhus, Denmark, followed by further testing after vegetative propagation since then. The inventor selected 'PKM06' on the basis of blue double flowers and compact growth habit.

Asexual reproduction of the new *Campanula* cultivar by terminal cuttings in Søhus, Denmark has demonstrated that the combination of characteristics as herein disclosed for the new cultivar are firmly fixed and retained through successive generations of asexual reproduction. The new cultivar reproduces true-to-type.

SUMMARY OF THE INVENTION

The following traits have been repeatedly observed and are determined to be the unique characteristics of 'PKM06'.

These characteristics in combination distinguish 'PKM06' as a new and distinct cultivar:

1. Upright plant habit with stiff stems.
2. Bushy globular plant form.
3. Vigorous growth habit, but still needing less chemical growth retardation.
4. Double light violet-blue flowers.

Plants of the cultivar 'PKM06' can be compared to the unpatented cultivar *Campanula* x *haydlodgensis* 'Blue Wonder' and 'PKM07' (U.S. Plant patent application Ser. No. 15/330,522). In side-by-side comparisons conducted by the inventor in Søhus, Denmark, plants of the instant cultivar 'PKM06' and plants of the cultivars 'Blue Wonder' and 'PKM07' differ in the following characteristics:

1. Plants of 'PKM06' have larger flowers than 'Blue Wonder'.
2. Plants of 'PKM06' have larger leaves than 'Blue Wonder'.
3. Plants of 'PKM06' have a more upright plant habit than 'Blue Wonder'.
4. Plants of 'PKM06' have lighter colored flowers than 'PKM07'.
5. Plants of 'PKM06' are less compact growing than 'PKM07'.

Data on plants of the parent varieties are no longer available for comparison with plants of the new cultivar *Campanula* 'PKM06'.

BRIEF DESCRIPTION OF THE PHOTOGRAPHS

The accompanying colored photographs illustrate the overall appearance of the new *Campanula* 'PKM06', showing the colors as true as it is reasonably possible to obtain in colored reproductions of this type. Colors in the photographs may differ slightly from the color values cited in the detailed botanical description, which more accurately describe the actual colors of 'PKM06'.

Figure 1:
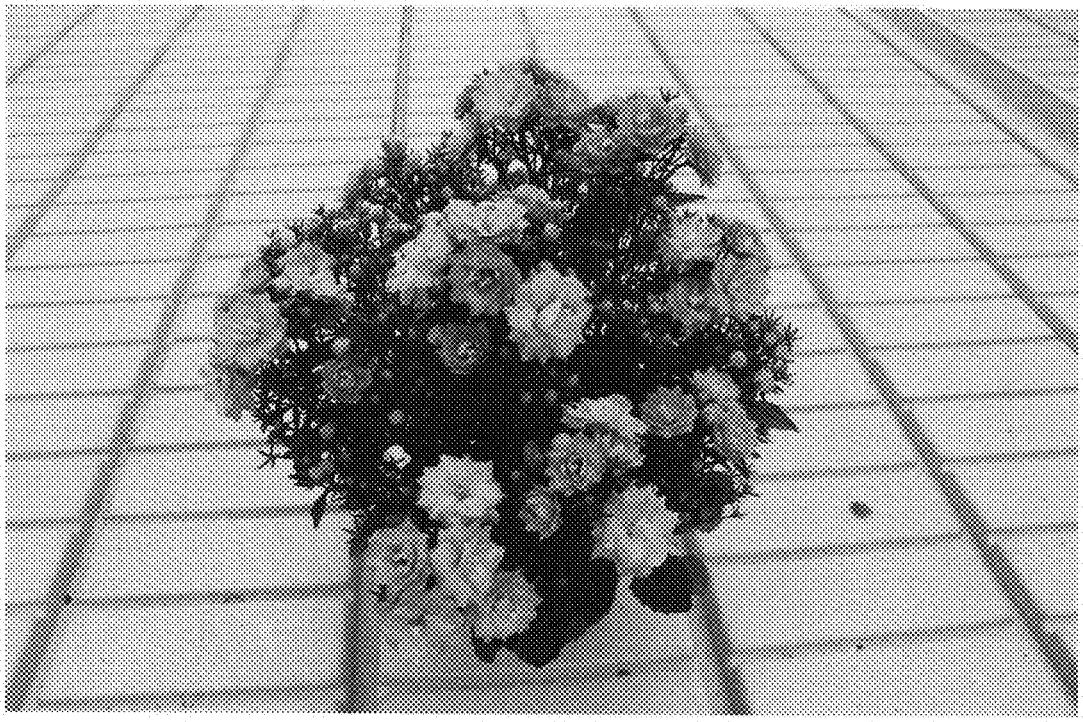

FIG. 1 comprises a side perspective view of a typical flowering plant of PKM06 grown in a 10.5 cm pot.

Figure 2:
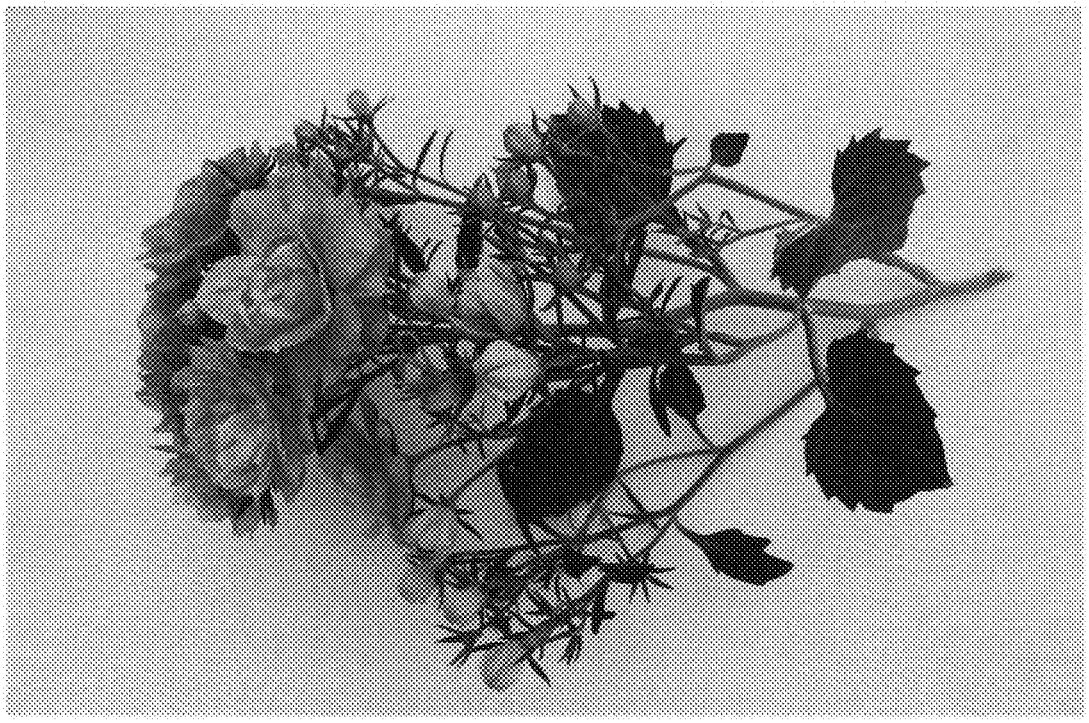

FIG. 2 comprises a close-up view of inflorescence of PKM06.

Figure 3:
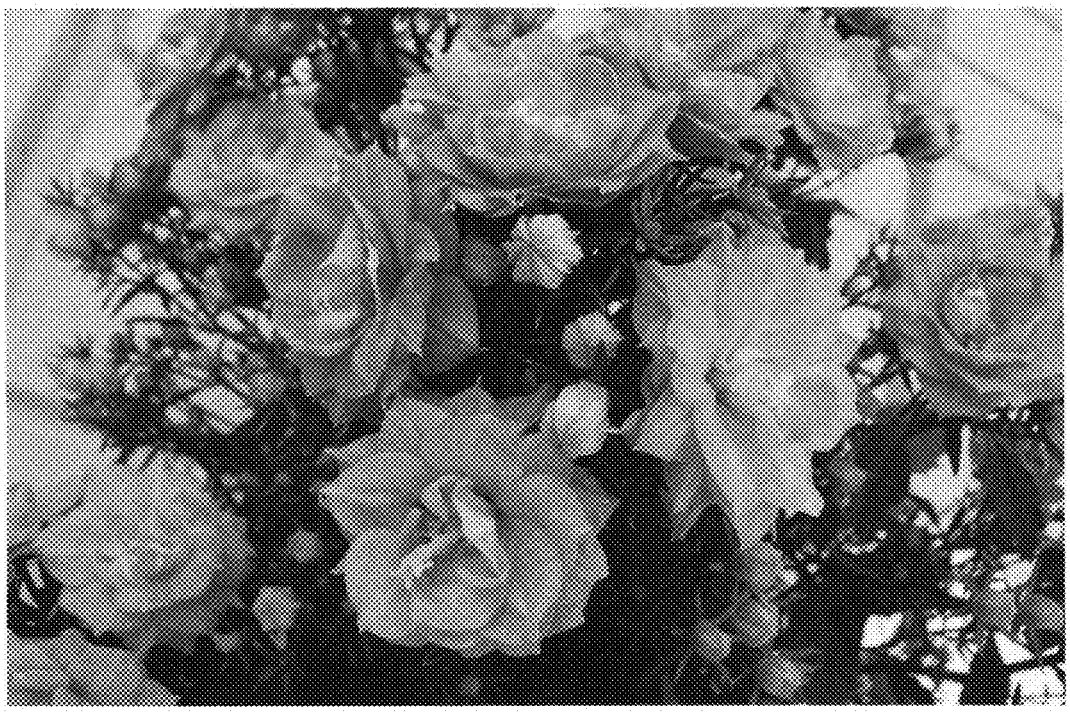

FIG. 3 comprises a close-up view of flowers of PKM06.

DETAILED BOTANICAL DESCRIPTION

The new *Campanula* 'PKM06' has not been observed under all possible environmental conditions. The phenotype of the new cultivar may vary with variations in environment such as growth regulator treatment, temperature, light intensity, day length, and fertility level without any variance in genotype.

The aforementioned photographs, together with the following observations, measurements and values describe plants of the new *Campanula* 'PKM06' as grown under greenhouse conditions.

The age of the 'PKM06' plants described is 3 months after propagation. Color references are made to The Royal Horticultural Society Colour Chart (R.H.S.), 5$^{th}$ edition, except where general colors of ordinary significance are used.

Classification:

*Botanical.*—*Campanula* interspecific hybrid.

Parentage:

*Female or seed parent.*—*Campanula* unpatented proprietary selection.

*Male or pollen parent.*—*Campanula* unpatented proprietary selection.

Propagation:

*Type cutting.*—Terminal vegetative cuttings.

*Time to initiate roots.*—About 10 to 14 days at 18 to 21° C. in tunnels in a greenhouse.

*Root description.*—Fine, well branched.

Plant description:

*Form.*—Upright plant habit. Double to filled wide campanulate flowers in panicles. Freely branching with lateral branches forming at every node.

*Crop time.*—After rooting, about 12 weeks are required to produce finished flowering plants in 10.5 cm pots.

*Plant height* (*from soil level to top of plant plane*).—About 16 cm. Depending on growth conditions.

*Plant width.*—About 25 cm. Depending on growth conditions.

*Stem.*—Color: green, RHS 138B. Form: Round, with recurrent leaf base.

*Vigor.*—Vigorous growth rate.

*Fruit/seed production.*—None observed.

Foliage description:

*Basal leaf shape.*—Single, dentate, cordiform, palmate venation.

*Leaf shape* (*upper part*).—Ovate.

*Leaf blade length.*—Up to 3 cm. Longest in the basal part of the plant.

*Leaf blade width.*—Up to 3 cm. Widest in the basal part of the plant.

*Petiole length.*—Up to 4 cm. Longest in the basal part of the plant.

*Apex.*—Obtuse.

*Base.*—Truncate to slightly cordate.

*Margin.*—Serrate; depth of indentation 2-3 mm.

*Texture.*—Glabrous, stiff.

*Glossiness.*—None.

*Pubescence.*—None.

*Color.*—Upper Surface, RHS N137A, Green. Lower Surface, RHS 138B (Green).

*Venation color.*—Similar or lighter green than leaf blade, but areas too small to determine R.H.S. values.

*Leaf blade rugosity.*—No rugosity between leaf veins.

Inflorescence description:

*Flower arrangement and shape.*—Single, upright, double to filled flowers in panicles with many flowers at lateral branches, flowers with star shaped sepals. Overall expression broadly campanulate; with some individual whorls more campanulate.

*Natural flowering season.*—Continuous throughout spring and summer. Season can be extended through long day treatments, no vernalization needed.

*Flower longevity.*—Individual flowers up to three weeks. Flowers persistent.

*Inflorescence size.*—Length: up to 17 cm.

*Flowers.*—Length: About 1.5 cm. Diameter: up to 3 cm. Layers of corollas (number of whorls): 3-5.

*Corolla.*—Length of tube: up to 10 mm. Length of lobe: up to 10 mm. Width of lobe: 10 mm. Tip of lobe: acute and twisted. Texture: Glabrous; no pubescence.

*Corolla color.*—Upper and Lower surfaces, RHS between 91A and 92B, violet-blue.

*Sepals.*—Arrangement: Free and sessile. Position: Changes with bud and flower development; sepals are full size early in corolla development, appearing stellate. Quantity per flower: 5. Length: 8 mm. Width: 1-2 mm. Overall shape: Triangular Tip: Acute. Margin: Entire. Color (mature and immature): Upper and lower surfaces: Green (areas too small to give R.H.S. values; nearly as leaf blade RHS 138B). Pedicel: Length: up to 3 cm. Diameter: up to 2 mm. Color: light green.

Reproductive organs:

*Gynoecium.*—Pistil and Stigma: Shape: often malformed. Color: White green tip before opening.

*Pollen.*—Amount: None to very little. Color: When present, yellow (amount too small to determine R.H.S. value).

I claim:

1. A new and distinct cultivar of *Campanula* plant named 'PKM06', as illustrated and described herein.

* * * * *